(12) United States Patent
Nakamura

(10) Patent No.: US 10,795,272 B2
(45) Date of Patent: Oct. 6, 2020

(54) TRIPHENYLAMINE DERIVATIVE, AND CHARGE TRANSPORT MATERIAL AND ELECTROPHOTOGRAPHIC PHOTORECEPTOR USING THE SAME

(71) Applicant: TAKASAGO INTERNATIONAL CORPORATION, Tokyo (JP)

(72) Inventor: Junji Nakamura, Chigasaki (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 295 days.

(21) Appl. No.: 16/068,033

(22) PCT Filed: Feb. 8, 2017

(86) PCT No.: PCT/JP2017/004586
§ 371 (c)(1),
(2) Date: Jul. 3, 2018

(87) PCT Pub. No.: WO2017/138566
PCT Pub. Date: Aug. 17, 2017

(65) Prior Publication Data
US 2020/0272064 A1 Aug. 27, 2020

(30) Foreign Application Priority Data
Feb. 8, 2016 (JP) .................... 2016-022109

(51) Int. Cl.
G03G 5/06 (2006.01)
C07C 217/92 (2006.01)
C07C 211/54 (2006.01)

(52) U.S. Cl.
CPC .......... *G03G 5/0614* (2013.01); *C07C 211/54* (2013.01); *C07C 217/92* (2013.01); *G03G 5/0618* (2013.01)

(58) Field of Classification Search
CPC ... C07C 217/92; C07C 211/54; G03G 5/0614; G03G 5/0618
See application file for complete search history.

(56) References Cited

U.S. PATENT DOCUMENTS

| | | | |
|---|---|---|---|
| 5,910,610 A | 6/1999 | Kobayashi et al. | |
| 5,989,765 A | 11/1999 | Kobayashi et al. | |
| 6,022,998 A | 2/2000 | Kawaguchi et al. | |
| 6,172,264 B1 | 1/2001 | Kobayashi et al. | |
| 2014/0213822 A1 | 7/2014 | Nakamura et al. | |

FOREIGN PATENT DOCUMENTS

| | | |
|---|---|---|
| JP | 03-149560 A | 6/1991 |
| JP | 08-295655 A | 11/1996 |
| JP | 09-034142 A | 2/1997 |
| JP | 10-114728 A | 5/1998 |
| JP | 2000-066419 A | 3/2000 |
| JP | 2000-239236 A | 9/2000 |
| JP | 2004-252066 A | 9/2004 |
| JP | 2005-154319 A | 6/2005 |
| JP | 2005-289877 A | 10/2005 |
| JP | 2008-063230 A | 3/2008 |
| JP | 2014-144927 A | 8/2014 |

OTHER PUBLICATIONS

International Searching Authority, International Search Report for PCT/JP2017/004586 dated Mar. 28, 2017 [PCT/ISA/210].

*Primary Examiner* — Jafar F Parsa
(74) *Attorney, Agent, or Firm* — Sughrue Mion, PLLC

(57) ABSTRACT

The present invention provides a triphenylamine derivative represented by general formula (1).

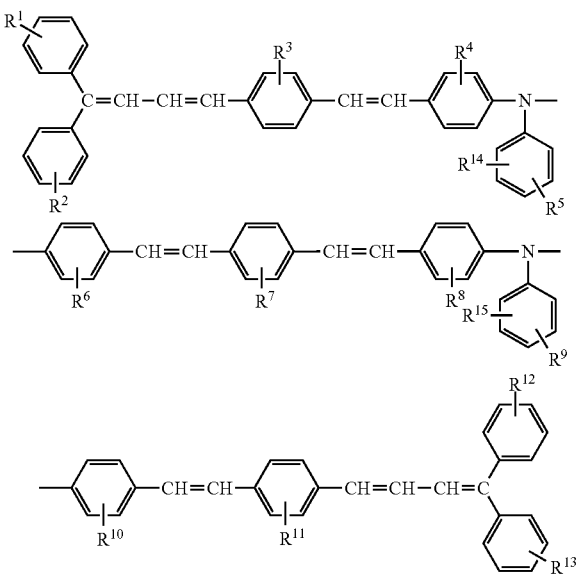

(In the formula, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ independently represent a hydrogen atom, a substituted or unsubstituted alkyl group or a substituted or unsubstituted alkoxy group).

6 Claims, No Drawings

TRIPHENYLAMINE DERIVATIVE, AND CHARGE TRANSPORT MATERIAL AND ELECTROPHOTOGRAPHIC PHOTORECEPTOR USING THE SAME

CROSS REFERENCE TO RELATED APPLICATIONS

This application is a National Stage of International Application No. PCT/JP2017/004586 filed Feb. 8, 2017, claiming priority based on Japanese Patent Application No. 2016-022109 filed Feb. 8, 2016.

TECHNICAL FIELD

The present invention provides a triphenylamine derivative as an organic photoconductor for obtaining an electrophotographic photoreceptor with high responsiveness.

BACKGROUND ART

Recently, there has been a remarkable advancement of information-processing system devices using the electrophotographic method. Especially, laser printers and digital copiers, which convert information into digital signals and record the information by using light, have achieved remarkable improvement in their printing quality and reliability. Moreover, they have been combined with speed-up techniques, and applied to laser printers and digital copiers capable of full-color printing.

As photoreceptors used for these laser printers, digital copiers, and the like of the electrophotographic method, photoreceptors using organic photoconductor materials (OPC) have been generally and widely used, because of the costs, productivity, pollution-free characteristics, and the like.

Recently, the reduction in diameter of the photoreceptor (the shortening of the time between exposure and development) with the speed-up of electrophotographic devices and the size-reduction of the devices has rendered the challenge to achieve high-speed responsiveness of a charge transport material in an electrophotographic photoreceptor further more important.

Tetraphenylbutadiene derivatives, hydrazone derivatives, triphenylamine derivative, and stilbene derivatives have been used as the charge transport material. Triphenylamine derivative having a 4,4-diphenyl-1,3-butadienyl group (for example, 4,4',4"-tris(4'",4'"-diphenyl-1'",3'"-butadienyl)triphenylamine (Japanese Patent Application Publication No. Hei 8-295655) and 4,4',4"-tris((4'"-(4'"",4'""-diphenyl-1'"", 3'"-butadienyl)styryl)phenyl)amine (Japanese Patent Application Publication No. 2014-144927)), whose conjugated systems are extended beyond those of stilbene derivatives, and the like exhibit high charge transport abilities. Likewise, many patent applications relating to butadienyl derivatives have been filed (Japanese Patent Application Publication Nos. Hei 9-34142, 2004-252066, 2005-289877, and 2008-63230). Moreover, patent applications relating to diamine derivatives having distyrylbenzene have also been filed (Japanese Patent Application Publication Nos. Hei 3-149560 and 2000-66419).

An ordinary charge transport layer is a solid solution film of approximately 10 to 30 μm in which such a low-molecular weight charge transport material is molecularly dispersed in a binder resin. In addition, a bisphenol-based polycarbonate resin, a polyarylate resin, or a copolymer thereof with another resin is used as the binder resin in most electrophotographic photoreceptors.

For film formation of the charge transport layer, the film is formed by dissolving the above-described binder resin and low-molecular weight charge transport material in an organic solvent. However, it cannot be said that the conventional low-molecular weight charge transport materials are sufficiently soluble in the binder resin and the organic solvent. Moreover, even though some conventional low-molecular weight charge transport materials are soluble and can be used to form films, charge transport layers using such low-molecular weight charge transport materials do not have sufficiently high carrier mobilities.

Accordingly, it cannot be said that it has been possible to obtain an electrophotographic photoreceptor which has excellent electrophotographic photoreceptor characteristics with a high sensitivity and a low residual potential, which makes it possible to form a charge transport layer by an easy film formation process, and which provides a stable film state.

SUMMARY OF INVENTION

An object of the present invention is to provide a charge transport material which has sufficiently satisfactory characteristics that are conventionally desired for a charge transport material for an electrophotographic photoreceptor, i.e., a charge transport material which has a good solubility in a binder resin, which is capable of forming a stable organic thin film at a high concentration, and further has a high responsiveness, i.e., a high carrier mobility, as well as to provide an electrophotographic photoreceptor using the charge transport material.

Under such circumstances, the present inventors have intensively studied various compounds, and consequently have found that a diamine derivative having a distyrylbenzene skeleton and further having a substituent with a diphenylbutadienylstyryl skeleton, namely, a novel triphenylamine derivative represented by the following general formula (1) can overcome the above-described problems, and specifically that the triphenylamine derivative of general formula (1) has good solubility in a binder resin, is resistant to crystal precipitation and pin-hole formation, and can exhibit a high carrier mobility, and also that a photoreceptor using the novel triphenylamine derivative has a high sensitivity and a low residual potential. These findings have led to the completion of the present invention:

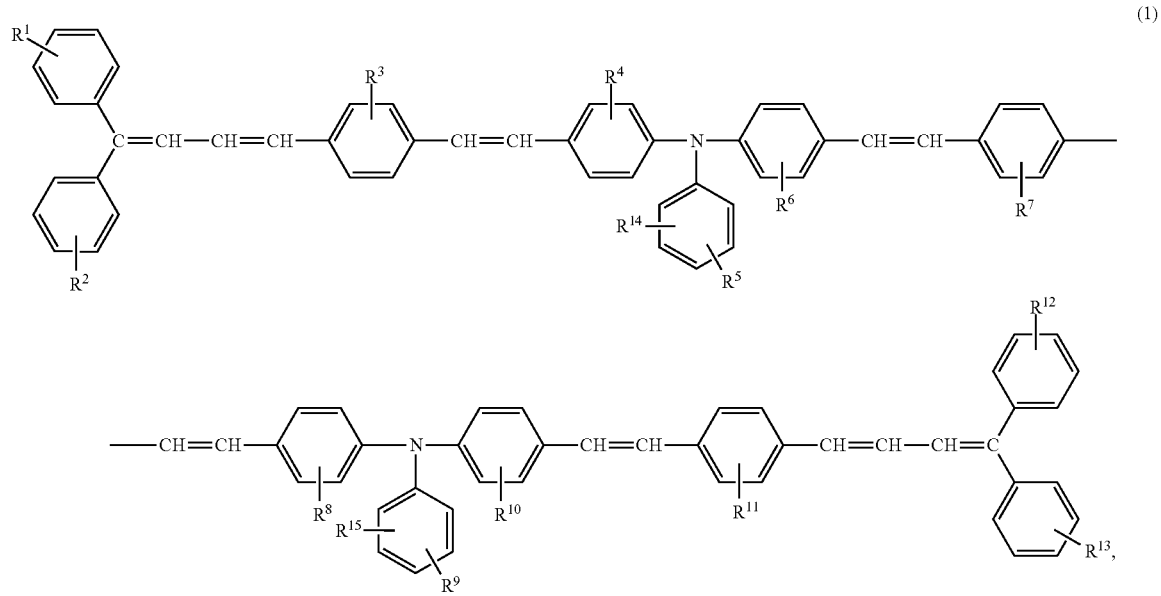

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ each independently represent a hydrogen atom, a substituted or unsubstituted alkyl group, or a substituted or unsubstituted alkoxy group.

Specifically, the present invention provides the following.

[1] A triphenylamine derivative represented by general formula (1):

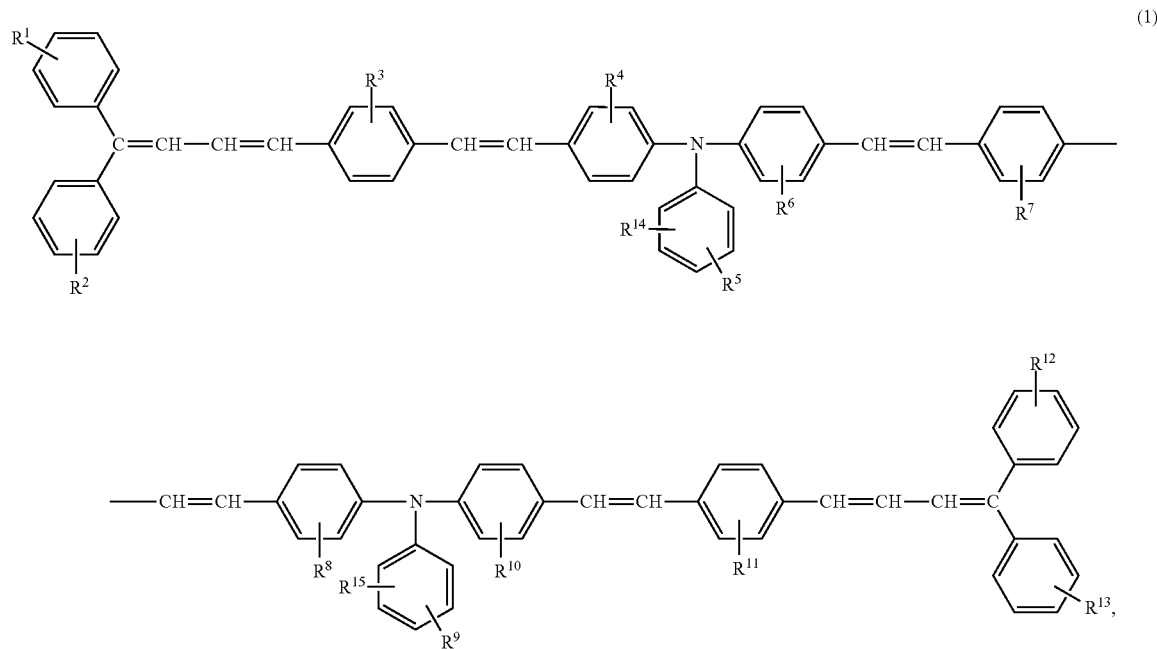

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ each independently represent a hydrogen atom, a substituted or unsubstituted alkyl group, or a substituted or unsubstituted alkoxy group.

[2] The triphenylamine derivative according to [1], which is represented by general formula (1'):

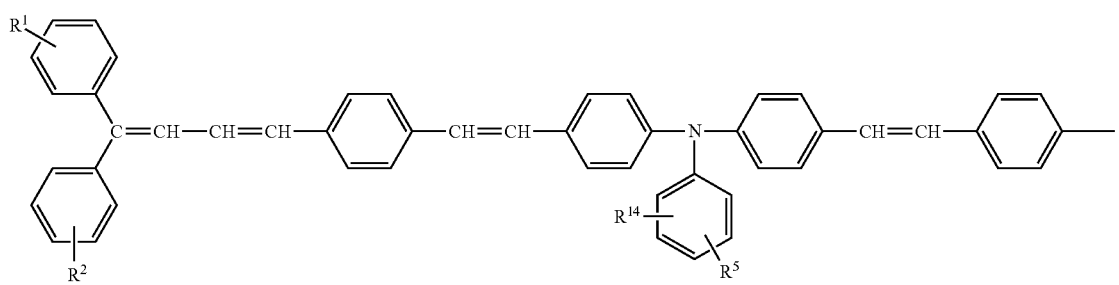
(1')

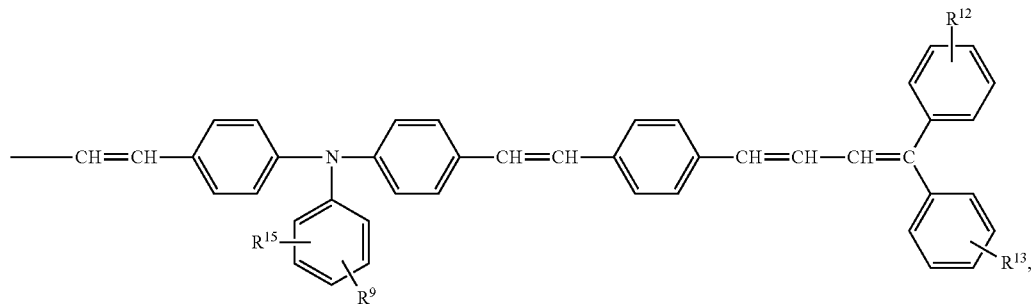

wherein $R^1$, $R^2$, $R^5$, $R^9$, $R^{12}$, $R^{13}$, $R^{14}$, and $R^{15}$ each independently represent a hydrogen atom, an alkyl group having 1 to 6 carbon atoms, or an alkoxy group having 1 to 6 carbon atoms.

[3] A charge transport material comprising the triphenylamine derivative according to [1] or [2].

[4] An electrophotographic photoreceptor comprising the charge transport material according to [3].

The novel triphenylamine derivative represented by the above-described general formula (1) of the present invention is useful as an electrically conductive material for organic electroluminescence, organic transistors, organic solar cells, and the like, and is particularly useful as a material for photoreceptors for electrophotography. Furthermore, the triphenylamine derivative of the present invention is extremely useful as a charge transport material for electrophotographic photoreceptors using an organic pigment or an inorganic pigment as a charge generation material, and, when used as an electrophotographic photoreceptor, it can exhibits high carrier mobility and has characteristics such as a high sensitivity and a low residual potential. Hence, the triphenylamine derivative of the present invention is industrially excellent.

DESCRIPTION OF EMBODIMENTS

Hereinafter, the present invention will be described in further detail.

A triphenylamine derivative of the present invention is represented by general formula (1):

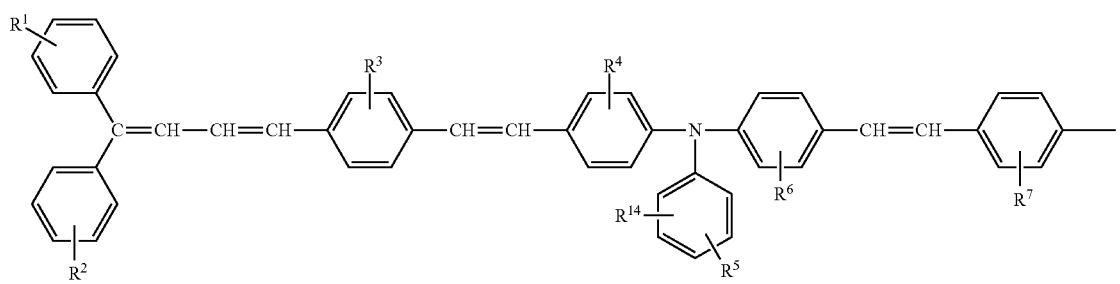
(1)

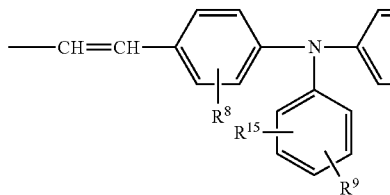
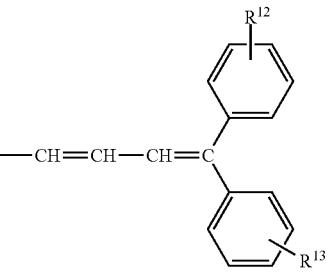

In general formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ each independently represent a hydrogen atom, a substituted or unsubstituted alkyl group, or a substituted or unsubstituted alkoxy group.

The substituted or unsubstituted alkyl group and the substituted or unsubstituted alkoxy group for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are described.

The alkyl group may be an alkyl group having 1 to 6 carbon atoms, such as a methyl group, an ethyl group, a propyl group, or a butyl group. The alkyl group may be preferably an alkyl group having 1 to 3 carbon atoms, and further preferably a methyl group.

The alkoxy group may be an alkoxy group having 1 to 6 carbon atoms, such as a methoxy group, an ethoxy group, a propoxy group, or a butoxy group. The alkoxy group may be preferably an alkoxy group having 1 to 3 carbon atoms, and further preferably a methoxy group.

Substituents on the alkyl group and the alkoxy group include alkoxy groups, phenyl groups, phenyloxy groups, and the like. The alkoxy groups include alkoxy groups having 1 to 6 carbon atoms, such as methoxy groups, ethoxy groups, propoxy groups, and butoxy groups.

Especially, $R^1$, $R^2$, $R^5$, $R^9$, $R^{12}$, $R^{13}$, $R^{14}$, and $R^{15}$ are preferably a hydrogen atom, a methyl group, or a methoxy group, and $R^3$, $R^4$, $R^6$, $R^7$, $R^8$, $R^{10}$, and $R^{11}$ are preferably a hydrogen atom.

The triphenylamine derivative represented by general formula (1) is preferably a triphenylamine derivative represented by general formula (1'):

(1')

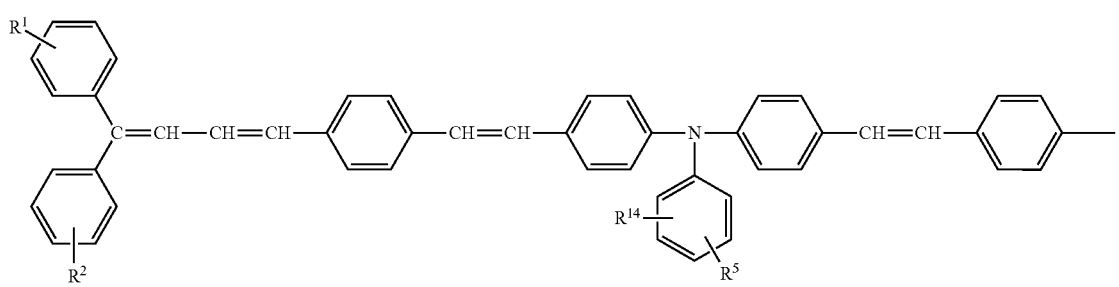

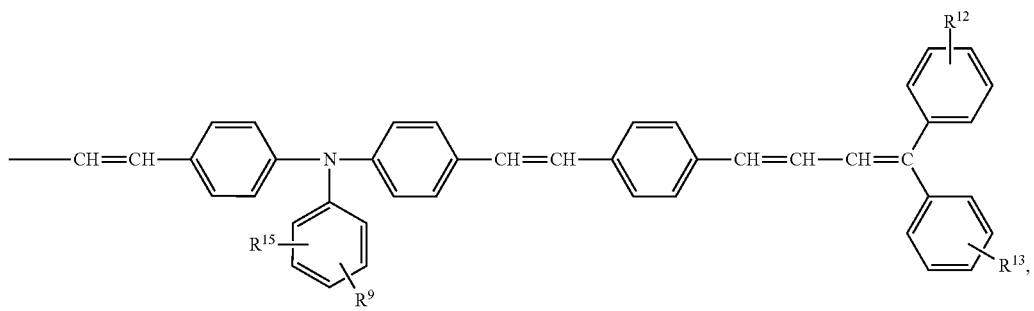

wherein $R^1$, $R^2$, $R^5$, $R^9$, $R^{12}$, $R^{13}$, $R^{14}$, and $R^{15}$ each independently represent a hydrogen atom, an alkyl group, or an alkoxy group.

In general formula (1'), specific description of $R^1$, $R^2$, $R^5$, $R^9$, $R^{12}$, $R^{13}$, $R^{14}$, and $R^{15}$ is as described above.

The triphenylamine derivative represented by general formula (1) has multiple double bonds. Preferably, some of these double bonds are in the trans configuration, and more preferably all the double bonds are in the trans configuration. However, the geometric isomerism of these double bonds is not limited thereto, but double bonds in the cis configuration may also be mixed in the triphenylamine derivative.

Preferred examples of general formula (1) include the following compounds; however, the present invention is not limited thereto.

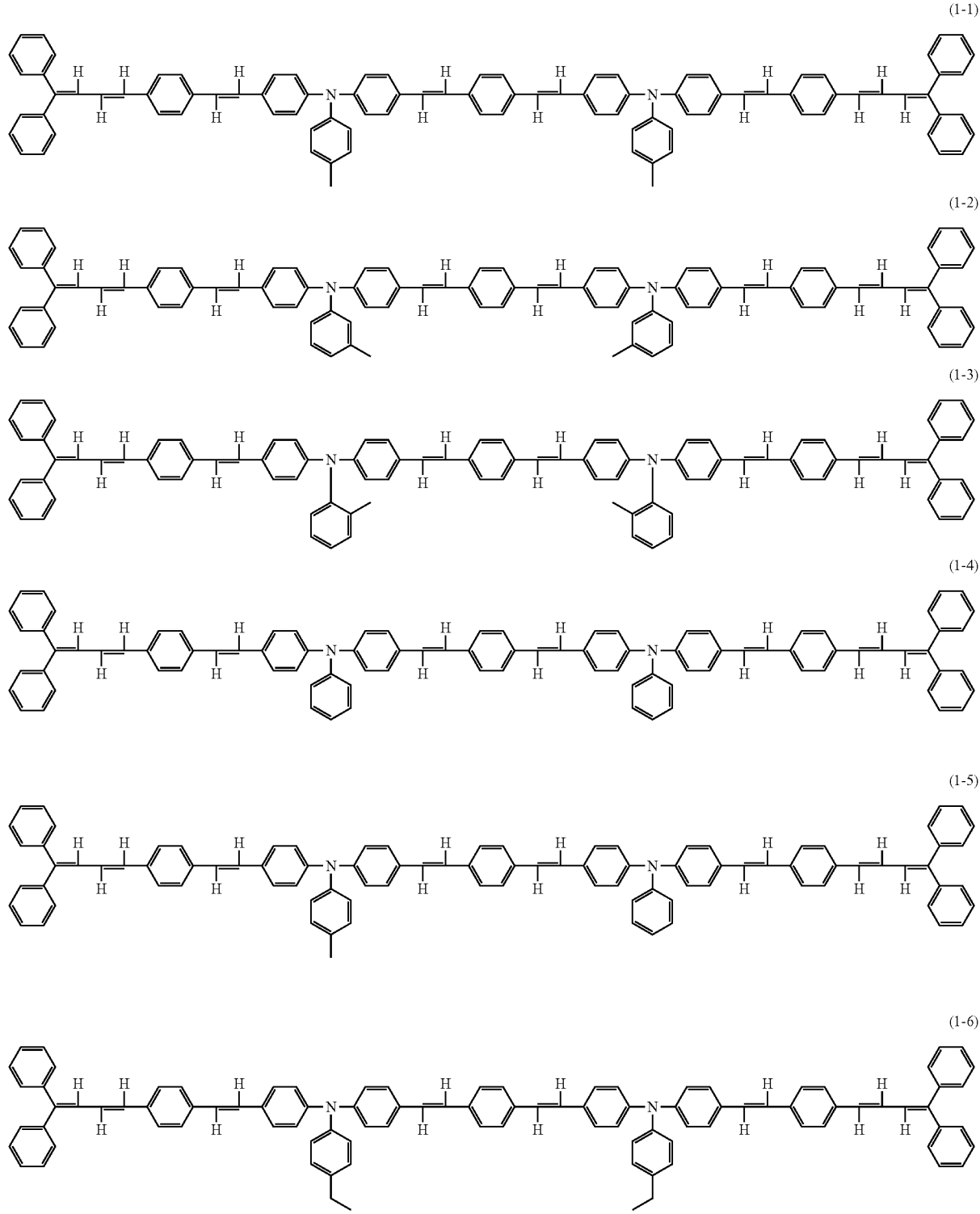

(1-7)
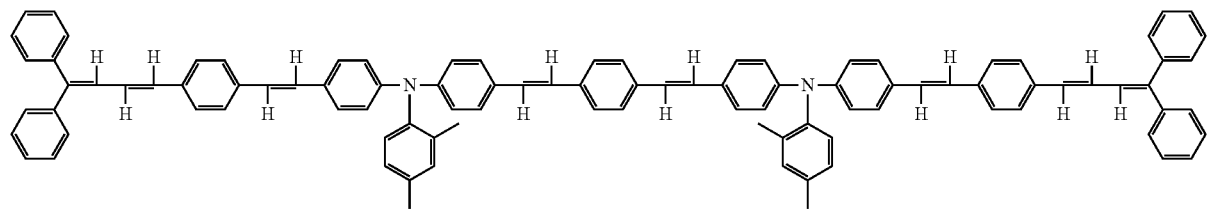
(1-8)
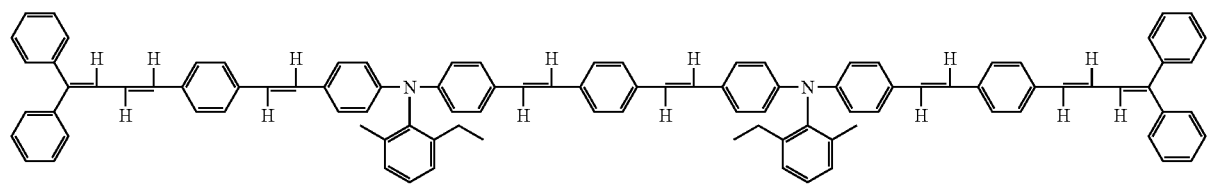
(1-9)
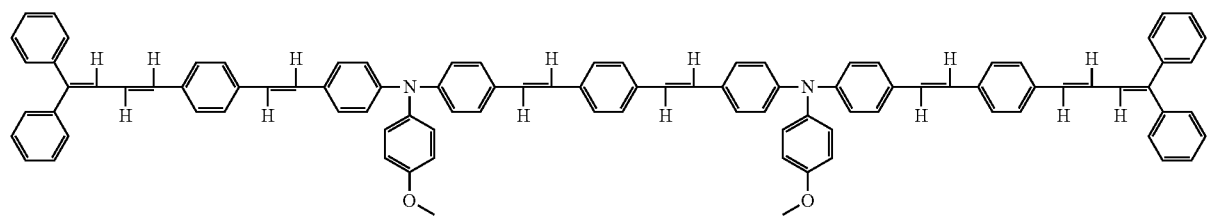
(1-10)
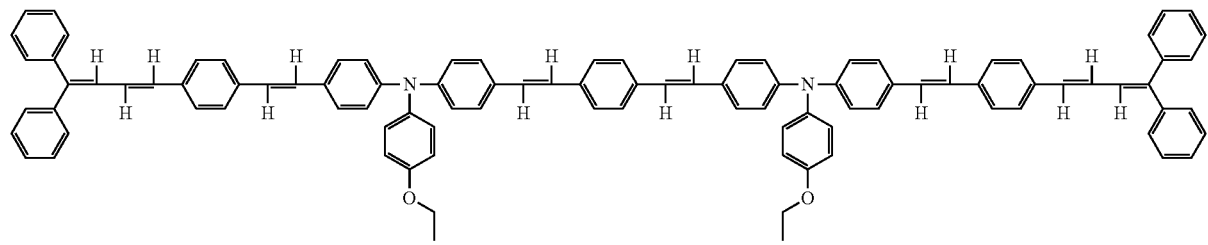
(1-11)
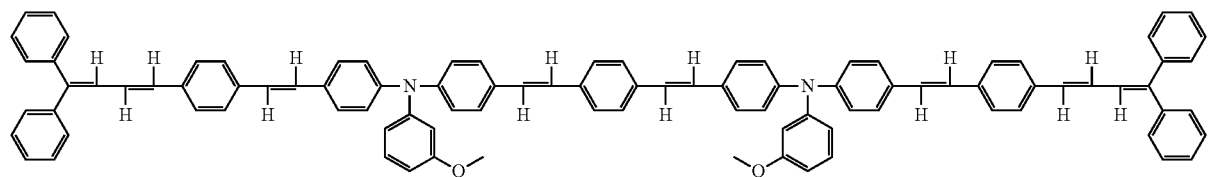
(1-12)
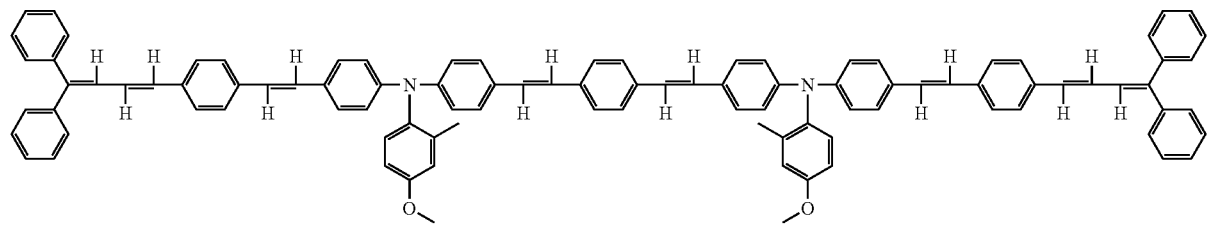

-continued
(1-13)
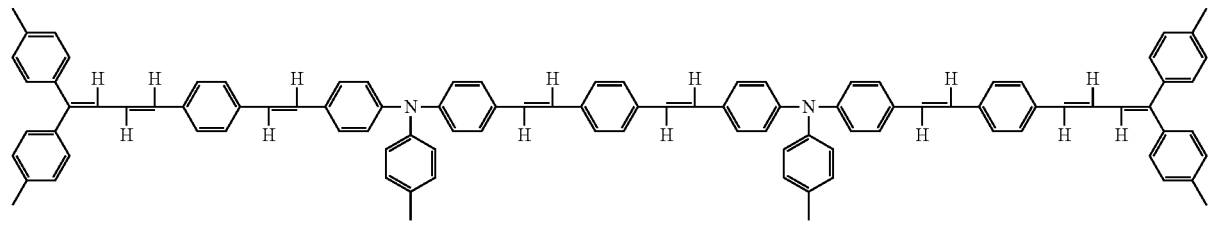
(1-14)
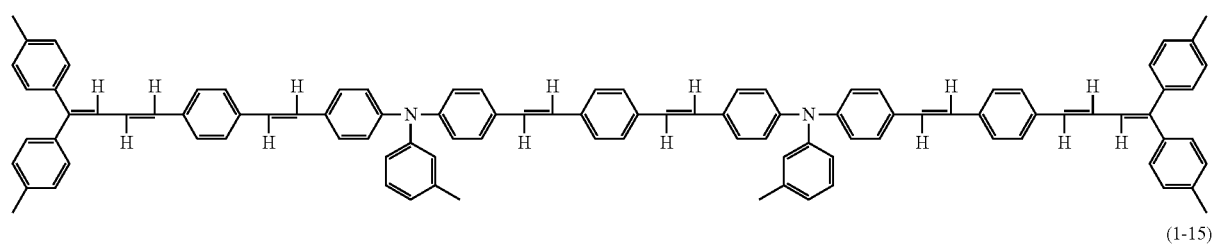
(1-15)
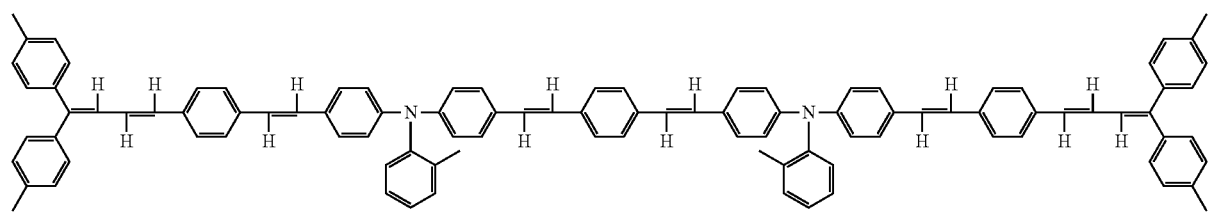
(1-16)
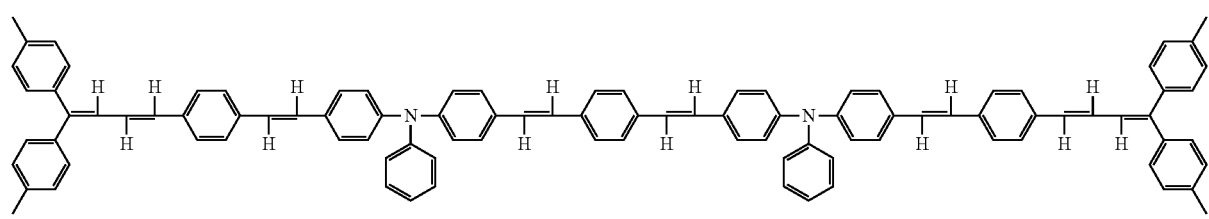
(1-17)
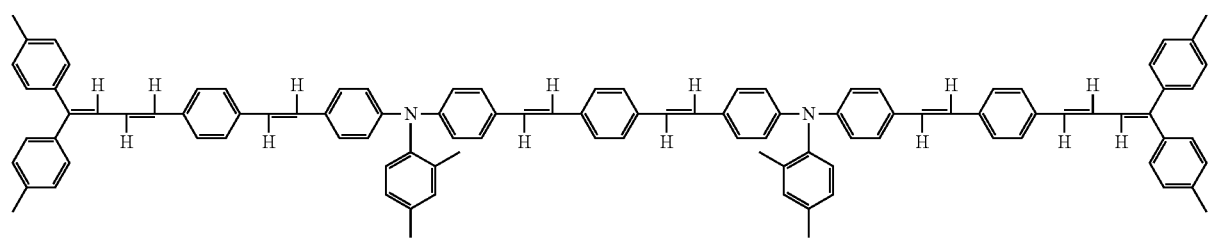
(1-18)

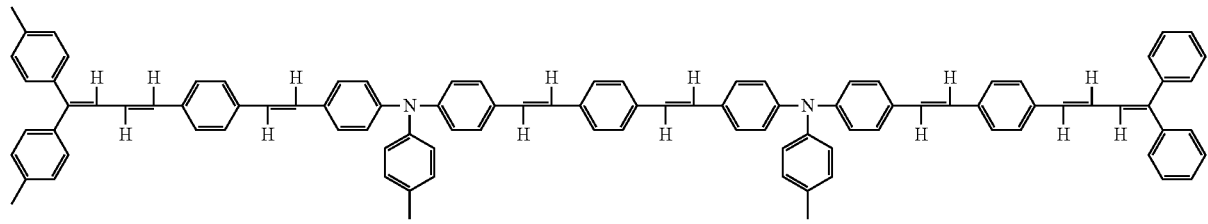

(1-19)

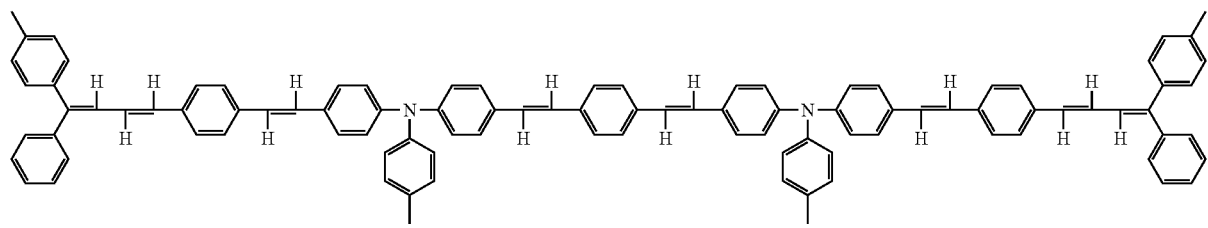

(1-20)

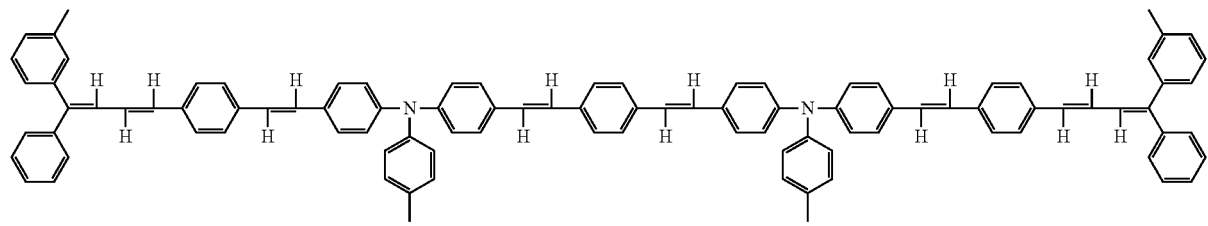

(1-21)

Of these examples, Compounds (1-1), (1-4), (1-7), (1-9), (1-13), and (1-17) are preferable.

The triphenylamine derivative represented by general formula (1) of the present invention can be synthesized, for example, as follows; however, the synthesis is not limited thereto.

General formula (1) of the present invention:

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ each independently represent a hydrogen atom, a substituted or unsubstituted alkyl group, or a substituted or unsubstituted alkoxy group, can be synthesized from a halogen compound represented by general formula (2) obtained by a method described in Japanese Patent Application Publication No. 2014-144927:

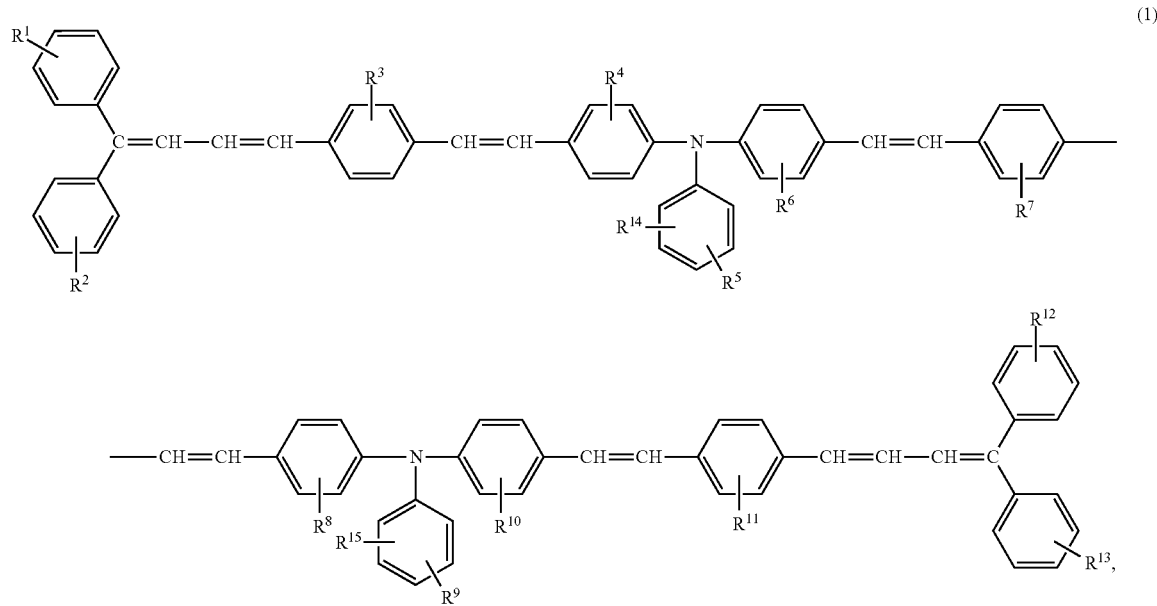

(1)

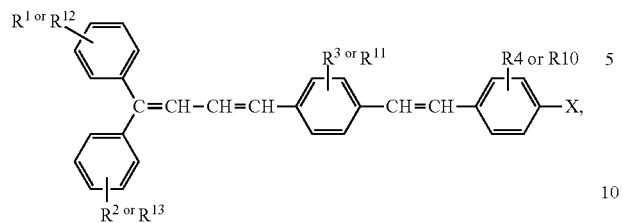
(2)
wherein X represents a chlorine atom, a bromine atom, or an iodine atom.
Specific description is given below:

Scheme
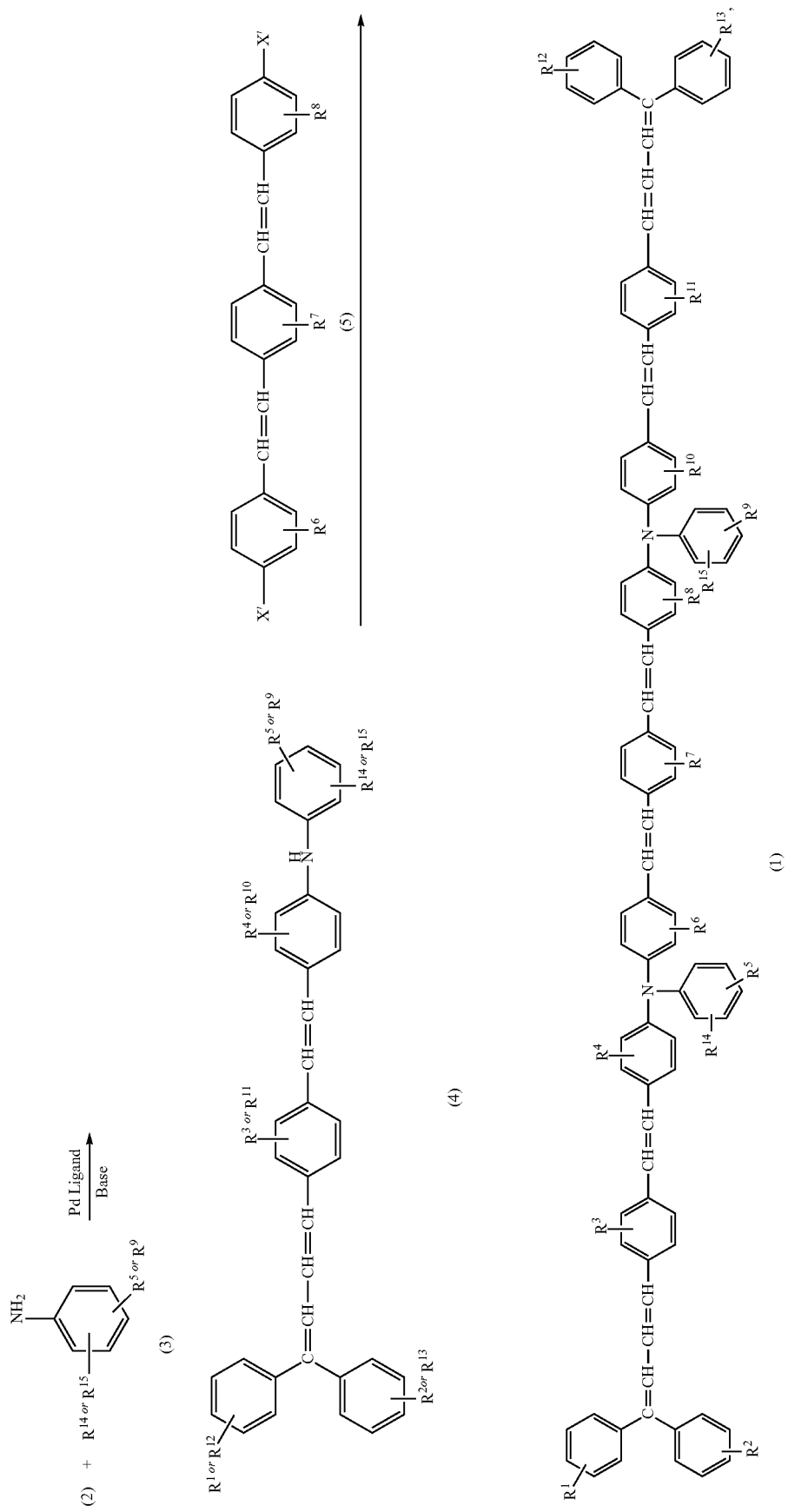

wherein X' represents a chlorine atom, a bromine atom, or an iodine atom.

In the scheme, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are the same as the definition for general formula (1).

A reaction of an aniline derivative (3) with the halogen compound represented by general formula (2) in the presence of a palladium complex and a base or in the presence of a metal such as Pd, a phosphorus atom-containing ligand, and a base according to a method of Buchwald et al. (J. Org. Chem., 2000, 65, 5327) makes it possible to obtain an intermediate represented by general formula (4). A further reaction with bis(halostyryl)benzene compound (5) makes it possible to synthesize general formula (1), which is the compound of the present invention.

Bases used in the synthetic method described above include sodium hydroxide, sodium amide, metal alkoxides such as sodium methoxide, sodium tert-butoxide, and potassium tert-butoxide, and the like. However, the base is not limited thereto.

Regarding the solvent used in the synthetic method described above, it is possible to use an alcohol such as methanol or ethanol, an ether such as 1,2-dimethoxyethane, diethyl ether, tetrahydrofuran, or dioxane, a hydrocarbon such as toluene or xylene, an aprotic polar solvent such as dimethyl sulfoxide, N,N-dimethylformamide, N,N-dimethylacetamide, or N-methylpyrrolidone, or a mixture of any of these solvents. However, the solvent is not limited thereto.

Palladium complexes used in the synthetic method described above include $PdCl_2$, $Pd(OAc)_2$, $[PdCl(allyl)]_2$, $Pd_2(dba)_3$, and the like. Here, "Ac" represents an acetyl group, and "dba" represents dibenzylideneacetone. However, the palladium complex is not limited thereto.

Phosphorus atom-containing ligands used in the synthetic method described above include triarylphosphine-based ligands such as triphenylphosphine and tri-o-tolylphosphine, trialkylphosphine-based ligands such as tri-t-butylphosphine and tricyclohexylphosphine, 2-phosphinobiphenyl-based ligands such as 2-(dicyclohexyl)phosphinobiphenyl, 2-(di-t-butylphosphino)biphenyl, 2-(dicyclohexylphosphino)-2',4',6'-tri-isopropyl-1,1'-biphenyl, and 2-(di-t-butylphosphino)-2'-(N,N-dimethylamino)biphenyl, olefin-substituted phosphine-based ligands such as 1,1-diphenyl-2-(dicyclohexylphosphino)propene and 1,1-diphenyl-2-(di-t-butylphosphino)propene, and cyclopropane ring-substituted phosphine-based ligands such as (di-t-butyl)(1-methyl-2,2-diphenylcyclopropyl)phosphine and (dicyclohexyl)(1-methyl-2,2-diphenylcyclopropyl)phosphine. However, the phosphorus atom-containing ligand is not limited thereto.

The method of synthesizing the novel triphenylamine derivative represented by general formula (1) of the present invention is not limited to the above-described coupling reaction. Specifically, the triphenylamine derivative can be produced by the Ullmann reaction or the like.

The novel triphenylamine derivative represented by general formula (1) of the present invention is useful as an electrically conductive material for organic transistors and organic solar cells, and is especially useful as a photoconductive material for photoreceptors for electrophotography.

Specifically, the electrophotographic photoreceptor of the present invention may be a so-called functionally-separated multilayer electrophotographic photoreceptor, in which functions of a photoreceptor layer are separated into a charge generation layer and a charge transport layer on an electrically conductive substrate, or a so-called single-layer electrophotographic photoreceptor, in which a single photoreceptor layer containing a charge generation agent and a charge transport agent is provided on an electrically conductive substrate.

In the functionally-separated multilayer electrophotographic photoreceptor, a charge transport layer using the triphenylamine derivative represented by general formula (1) of the present invention as a charge transport agent is formed by direct vapor deposition of the triphenylamine derivative represented by general formula (1) of the present invention onto an electrically conductive substrate or a charge generation layer, or by applying a solution, which has been prepared by dissolving the triphenylamine derivative represented by general formula (1) of the present invention and a binder resin in a suitable solvent, onto an electrically conductive substrate or a charge generation layer, followed by drying.

On the other hand, the single-layer electrophotographic photoreceptor is formed by applying a solution, which has been prepared by dissolving or dispersing a charge generation agent, the triphenylamine derivative represented by general formula (1) of the present invention, and the like together with a binder resin in a suitable solvent, onto an electrically conductive substrate, followed by drying. Note that the single-layer electrophotographic photoreceptor may contain an electron transport material, if necessary.

Examples of the binder resin include insulating polymers such as polyacrylates, polymethacrylates, polyamides, acrylic resins, acrylonitrile resins, methacrylic resins, vinyl chloride resins, vinyl acetate resins, phenolic resins, epoxy resins, polyesters, polyarylate (aromatic polyester) resins, alkyd resins, polycarbonates, polyurethanes, polystyrenes, copolymers thereof, and the like. Besides these insulating polymers, it is also possible to use organic photoconductive polymers such as polyvinylcarbazole, polyvinylanthracene, and polyvinylene. Of these binder resins, it is particularly preferable to use a polyarylate resin or a polycarbonate.

Examples of preferably usable polyarylate resins include polyarylate resins manufactured by Unitika Ltd. under the product name of U series, copolymer polyarylate resins, and the like. Preferably usable polycarbonates include polycarbonate resins of bisphenol A (2,2-bis(4-hydroxyphenyl)propane) (for example, Iupilon E series manufactured by Mitsubishi Gas Chemical Company, Inc.), polycarbonate resins of bisphenol Z (1,1-bis(4-hydroxyphenyl)cyclohexane) (for example, Panlite series manufactured by Teijin Chemicals Ltd. and Iupilon Z series manufactured by Mitsubishi Gas Chemical Company, Inc.), bisphenol/biphenol copolymer polycarbonate resins disclosed in Japanese Patent Application Publication No. Hei 4-179961, and the like.

In addition to the above-described polycarbonates, polycarbonates disclosed in Japanese Patent Application Publication Nos. Hei 6-214412 and Hei 6-222581 can be used.

Furthermore, polysiloxane copolymer polycarbonate resins can also be used, which are binder resins excellent in slip properties and wear resistance disclosed in Japanese Patent Application Publication Nos. Hei 5-297620 and Hei 05-158249.

The blending ratio of the binder resin with the triphenylamine derivative represented by general formula (1) of the present invention is such that all the charge transport substance including the triphenylamine derivative represented by general formula (1) of the present invention can be added at an ratio of 1 to 1000 parts by weight, preferably 30 to 500 parts by weight, and further preferably 40 to 200 parts by weight per 100 parts by weight of the binder resin. Moreover, the triphenylamine derivative represented by general formula (1) of the present invention can be added at a ratio of 0.1 to 100% by weight, preferably 1 to 100% by weight, and further preferably 10 to 100% by weight, relative to the total weight of all the charge transport substances.

The solvent used is not particularly limited, and organic solvents can be used. The organic solvents include alcohols such as methanol, ethanol, and isopropanol, ketones such as acetone, methyl ethyl ketone, and cyclohexanone, amides such as N,N-dimethylformamide and N,N-dimethylacetamide, sulfoxides such as dimethyl sulfoxide, ethers such as tetrahydrofuran, dioxane, and ethylene glycol dimethyl ether, esters such as ethyl acetate and methyl acetate, aliphatic halogenated hydrocarbons such as methylene chloride, chloroform, 1,2-dichloroethane, dichloroethylene, carbon tetrachloride, and trichloroethylene, aromatic compounds such as benzene, toluene, xylene, chlorobenzene, and dichlorobenzene. One of these solvents can be used alone, or a mixture of any ones of these solvents can be used.

As the electrically conductive substrate used for the photoreceptor of the present invention, a foil or plate of a metal such as copper, aluminum, silver, iron, zinc, or nickel, or an alloy thereof shaped into a sheet or a drum is used. Alternatively, the electrically conductive substrate used is one obtained by vacuum vapor deposition or electrolytic plating of any of these metals onto a plastic film or cylinder or the like, or an electrically conductive substrate, or one obtained by providing a layer of an electrically conductive compound such as an electrically conductive polymer, indium oxide, or tin oxide on a substrate of glass, paper, or a plastic film by application or vapor deposition.

The application can be conducted by a coating method such as the dip coating method, the spray coating method, the spinner coating method, the wire-bar coating method, the blade coating method, the roller coating method, or the curtain coating method.

For the drying, a method in which a drying at room temperature is followed by heat drying is preferable. The heat drying is preferably conducted at a temperature of 30 to 200° C. in a range of 5 minutes to 5 hours with or without blowing.

Moreover, as a charge transport material other than the triphenylamine derivative represented by general formula (1) of the present invention, an additional charge transport material and various additives can be added to and used in the electrophotographic photoreceptor of the present invention, if necessary. Examples of the additional charge transport material include hydrazone compounds described in U.S. Pat. No. 4,150,987, Japanese Patent Application Publication No. Sho 61-23154 etc., triphenylamine dimers described in Japanese Examined Patent Application Publication No. Sho 58-32372 etc., distyryl compounds described in U.S. Pat. No. 3,873,312 etc., substituted or unsubstituted tetraphenylbutadiene-based compounds, α-phenylstilbene, substituted or unsubstituted polyvinylcarbazoles, substituent or unsubstituted triphenylamines, substituent or unsubstituted triphenylmethanes, and the like.

Moreover, the examples also include oxadiazole-based compounds such as 2,5-di(4-methylaminophenyl)-1,3,4-oxadiazole, organic polysilane compounds, pyrazoline-based compounds such as 1-phenyl-3-(p-dimethylaminophenyl) pyrazoline, nitrogen-containing cyclic compounds such as indole-based compounds, oxazole-based compounds, isoxazole-based compounds, thiazole-based compounds, thiadiazole-based compounds, imidazole-based compounds, pyrazole-based compounds, and triazole-based compounds, condensed polycyclic compounds, and the like.

One of these charge transport materials may be used alone, or two or more thereof may be used in combination; however, the charge transport materials are not limited thereto.

Examples of the various additives include biphenylene-based compounds (for example, those described in Japanese Patent Application Publication No. Hei 6-332206), m-terphenyl, plasticizers such as dibutyl phthalate, surface lubricants such as silicone oils, graft-type silicone polymers, and various fluorocarbons, potential stabilizers such as dicyanovinyl compounds and carbazole derivatives, mono-phenol-based antioxidants such as 2-tert-butyl-4-methoxyphenol and 2,6-di-tert-butyl-4-methylphenol, bisphenol-based antioxidants, amine-based antioxidants such as 4-diazabicyclo[2,2,2]octane, salicylic acid-based antioxidants, tocopherols, and the like.

When the electrophotographic photoreceptor of the present invention is a functionally-separated multilayer electrophotographic photoreceptor, the film thickness of the obtained charge transport layer is not particularly limited, and is preferably 5 to 50 μm, and more preferably 10 to 30 μm. When electrically connected to a charge generation layer, the charge transport layer obtained as described above has functions of receiving carriers injected from the charge generation layer and also transporting these carriers across the charge transport layer to the surface opposite to the surface in contact with the generation layer in the presence of an electric field. Here, the charge transport layer may be stacked as an upper layer of the charge generation layer, or stacked as a lower layer of the charge generation layer; however, it is desirable that the charge transport layer be stacked as an upper layer of the charge generation layer. If necessary, a protective layer may be applied and formed on the photoreceptor layer prepared as described above. In addition, it is also possible to provide an underlayer having a barrier function and an adhesive function between the electrically conductive substrate and the photoreceptor layer. Materials for forming the underlayer include polyvinyl alcohol, nitrocellulose, casein, ethylene-acrylic acid copolymer, polyamides such as nylon, polyurethane, gelatin, aluminum oxide, and the like. The film thickness of the underlayer is preferably 0.1 to 5 μm, and more preferably 0.5 to 3 μm.

When the electrophotographic photoreceptor of the present invention is a single-layer electrophotographic photoreceptor, the film thickness of the obtained photoreceptor layer is not particularly limited, and is preferably 5 to 100 μm, and more preferably 10 to 50 μm. The photoreceptor layer obtained as described above has a function of transporting the electric charge generated from a charge generation agent to the electrically conductive substrate and to the surface in the presence of an electric field. If necessary, a protective layer can be applied and formed on the photoreceptor layer prepared as described above. In addition, it is also possible to provide an underlayer having a barrier function and an adhesive function between the electrically conductive substrate and the photoreceptor layer. As materials for forming the underlayer, the same materials described for the multilayer electrophotographic photoreceptor can be used.

For the charge generation layer, various organic pigments can be used.

The organic pigments include C. I. Pigment Blue 25 (Color Index CI 21180), C. I. Pigment Red 41 (CI 21200), C. I. Acid Red 52 (CI 45100), C. I. Basic Red 3 (CI 45210), azo pigments such as azo pigments having a carbazole skeleton (Japanese Patent Application Publication No. Sho 53-95033), azo pigments having a distyrylbenzene skeleton (Japanese Patent Application Publication No. Sho 53-133445), azo pigments having a triphenylamine skeleton (Japanese Patent Application Publication No. Sho 53-132347), azo pigments having a dibenzothiophene skeleton (Japanese Patent Application Publication No. Sho 54-21728), azo pigments having an oxadiazole skeleton (Japanese Patent Application Publication No. Sho 54-12742), azo pigments having a fluorenone skeleton (Japanese Patent Application Publication No. Sho 54-22834), azo pigments having a bisstilbene skeleton (Japanese Patent Application Publication No. Sho 54-17733), azo pigments having a distyryloxadiazole skeleton (Japanese Patent Application Publication No. Sho 54-2129), azo pigments having a distyrylcarbazole skeleton (Japanese Patent Application Publication No. Sho 54-14967), and azo pigments having a benzanthrone skeleton, and the like. Further, the organic pigments include phthalocyanine-based pigments such as C. I.

Pigment Blue 16 (CI 74100), Y-type oxotitanium phthalocyanine (Japanese Patent Application Publication No. Sho 64-17066), A(β)-type oxotitanium phthalocyanine, B(α)-type oxotitanium phthalocyanine, I-type oxotitanium phthalocyanine (Japanese Patent Application Publication No. Hei 11-21466), II-type chlorogallium phthalocyanine (Iijima et al., The Chemical Society of Japan 67th Spring Annual Meeting, 1B4, 04 (1994)), V-type hydroxygallium phthalocyanine (Daimon et al., The Chemical Society of Japan 67th Spring Annual Meeting, 1B4, 05 (1994)), and X-type metal-free phthalocyanine (U.S. Pat. No. 3,816,118), indigo-based pigments such as C.I. Vat Brown 5 (CI 73410) and C.I. Vat Dye (CI 73030), perylene pigments such as Algo scarlet B (manufactured by Bayer AG) and Indanthrene scarlet R (manufactured by Bayer AG), and the like.

Note that one of these materials may be used alone, or two or more thereof may be used in combination.

It is also possible to use inorganic pigments such as selenium, selenium-tellurium, cadmium sulfide, and α-silicon.

Any charge generation agent other than those described above can also be used, as long as the material absorbs light and generates electric charges at a high efficiency.

As described above, an electrophotographic photoreceptor comprising the triphenylamine derivative represented by general formula (1) of the present invention can be obtained.

EXAMPLES

Hereinafter, the present invention will be described in further detail based on Examples; however, the present invention is not limited to these Examples. Note that measuring instruments and measurement conditions used in Examples are shown below.
(1) $^1$H-NMR instruments; DRX-500 model instruments (500 MHz) manufactured by Bruker Corporation Internal standard substance; tetramethylsilane Measured in deuterated chloroform
(2) Mass spectrometer; JMS-T100GCV manufactured by JEOL Ltd.

Example 1

Synthesis of Compound (1-1)

Under a nitrogen atmosphere, 8.38 g (20 mmol) of 4-(4'-(4",4"-diphenyl-1",3"-butadienyl)styryl)chlorobenzene, 2.4 g (25 mmol) of sodium tert-butoxide, 2.1 g (20 mmol) of p-toluidine, 3.7 mg (0.010 mmol) of [PdCl(allyl)]$_2$, and 16 mg (0.040 mmol) of 1,1-diphenyl-2-(dicyclohexylphosphino)propene were added to 40 ml of xylene, followed by heating to 100° C. After stirring for 3 hours, water was added, then toluene was added and the organic layer was extracted. After washing with water, the organic layer was concentrated, followed by recrystallization using a toluene-methanol solvent, to obtain 8.0 g of a yellow solid. A 7.5 g portion of the yellow solid was mixed with 40 ml of xylene, and 1.8 g (19 mmol) of sodium tert-butoxide, 2.6 g (7.5 mmol) of 1,4-bis(4-chlorostyryl)benzene, 2.7 mg (0.008 mmol) of [PdCl(allyl)]$_2$, and 12 mg (0.030 mmol) of 1,1-diphenyl-2-(dicyclohexylphosphino)propene were further added, followed by heating to 120° C. After stirring for 8 hours, water was added, then toluene was added and the organic layer was extracted. After washing with water, the organic layer was concentrated, followed by recrystallization using a toluene-ethyl acetate solvent, to obtain 5.0 g of a yellow solid (Compound 1-1). The yield was 43%.

1H NMR (CDCl$_3$): δ; 2.33 (s, 6H), 6.69-6.76 (m, 2H), 6.86-7.16 (m, 30H), 7.23-7.32 (m, 16H), 7.35-7.45 (m, 22H).

FD-MS([M]+): found m/z 1256.6032 [C96H76N2]+ (calculated; 1256.6008, 1.87 ppm)

mp 178-180° C.

Example 2

Synthesis of Compound (1-4)

Under a nitrogen atmosphere, 5.2 g (12 mmol) of 4-(4'-(4",4"-diphenyl-1",3"-butadienyl)styryl)chlorobenzene, 2.9 g (30 mmol) of sodium tert-butoxide, 1.1 g (12 mmol) of aniline, 4.4 mg (0.012 mmol) of [PdCl(allyl)]$_2$, and 19 mg (0.048 mmol) of 1,1-diphenyl-2-(dicyclohexylphosphino) propene were added to 40 ml of xylene, followed by heating to 100° C. After stirring for 2 hours, 2.1 g (6.0 mmol) of 1,4-bis(4-chlorostyryl)benzene was added, followed by further heating to 110° C. After stirring for 2 hours, water was added, then toluene was added and the organic layer was extracted. After washing with water, the organic layer was concentrated, followed by recrystallization using a toluene-ethyl acetate solvent, to obtain 5.3 g of a yellow solid (Compound 1-4). The yield was 72%.

1H NMR (CDCl$_3$): δ; 6.69-6.76 (m, 2H), 6.89-7.13 (m, 30H), 7.23-7.32 (m, 22H), 7.36-7.45 (m, 18H), 7.47 (s, 4H).

FD-MS([M]+): found m/z 1228.5647 [C94H72N2]+(calculated; 1228.5695, -3.95 ppm)

mp 162-164° C.

Example 3

Synthesis of Compound (1-7)

Under a nitrogen atmosphere, 6.3 g (15 mmol) of 4-(4'-(4",4"-diphenyl-1",3"-butadienyl)styryl)chlorobenzene, 1.8 g (19 mmol) of sodium tert-butoxide, 2.0 g (17 mmol) of 2,4-dimethylaniline, 5.5 mg (0.015 mmol) of [PdCl(allyl)]$_2$, and 23 mg (0.060 mmol) of 1,1-diphenyl-2-(dicyclohexylphosphino)propene were added to 40 ml of xylene, followed by heating to 100° C. After stirring for 2 hours, water was added, then toluene was added and the organic layer was extracted. After washing with water, the organic layer was concentrated, followed by recrystallization using a toluene-methanol solvent, to obtain 5.3 g of a yellow solid. A 5.2 g portion of the yellow solid was mixed with 40 ml of xylene, and 1.2 g (13 mmol) of sodium tert-butoxide, 1.8 g (5.0 mmol) of 1,4-bis(4-chlorostyryl)benzene, 1.8 mg (0.005 mmol) of [PdCl(allyl)]$_2$, and 7.8 mg (0.020 mmol) of 1,1-diphenyl-2-(dicyclohexylphosphino)propene were further added, followed by heating to 110° C. After stirring for 4 hours, water was added, then toluene was added and the organic layer was extracted. After washing with water, the organic layer was concentrated, and impurities were removed by silica gel column chromatography to obtain 4.5 g of a yellow solid (Compound (1-7)). The yield was 48%.

1H NMR (CDCl$_3$): δ; 2.00 (s, 6H), 2.35 (s, 6H), 6.69-6.76 (m, 2H), 6.89-7.08 (m, 26H), 7.15-7.43 (m, 36H), 7.44 (s, 4H).

FD-MS([M]+): found m/z 1284.6371 [C98H88N2]+(calculated; 1284.6321, 3.85 ppm)

mp 161-163° C.

Example 4

Synthesis of Compound (1-9)

Under a nitrogen atmosphere, 8.4 g (20 mmol) of 4-(4'-(4'',4''-diphenyl-1'',3''-butadienyl)styryl)chlorobenzene, 2.4 g (25 mmol) of sodium tert-butoxide, 2.5 g (20 mmol) of p-methoxyaniline, 3.7 mg (0.010 mmol) of [PdCl(allyl)]$_2$, and 16 mg (0.040 mmol) of 1,1-diphenyl-2-(dicyclohexylphosphino)propene were added to 40 ml of xylene, followed by heating to 100° C. After stirring for 3 hours, water was added, then toluene was added and the organic layer was extracted. After washing with water, the organic layer was concentrated, followed by recrystallization using a toluene-methanol solvent, to obtain 5.6 g of a yellow solid. A 5.2 g portion of the yellow solid was mixed with 40 ml of xylene, and 1.2 g (13 mmol) of sodium tert-butoxide, 1.8 g (5.0 mmol) of 1,4-bis(4-chlorostyryl)benzene, 3.6 mg (0.010 mmol) of [PdCl(allyl)]$_2$, and 16 mg (0.040 mmol) of 1,1-diphenyl-2-(dicyclohexylphosphino)propene were further added, followed by heating to 120° C. After stirring for 4 hours, water was added, then toluene was added and the organic layer was extracted. After washing with water, the organic layer was concentrated, followed by recrystallization using a toluene-ethyl acetate solvent, to obtain 4.7 g of a yellow solid (Compound 1-9). The yield was 41%.

1H NMR (CDCl$_3$): δ; 3.81 (s, 6H), 6.69-6.76 (m, 2H), 6.84-7.11 (m, 28H), 7.23-7.33 (m, 18H), 7.34-7.40 (m, 14H), 7.41-7.46 (m, 8H).

FD-MS([M]+): found m/z 1288.5935 [C96H76N2O2]+ (calculated; 1288.5907, 2.18 ppm)

mp 222-224° C.

Example 5

Synthesis of Compound (1-13)

Under a nitrogen atmosphere, 9.2 g (21 mmol) of 4-(4'-(4'',4''-bis(4'''-methylphenyl)-1'',3''-butadienyl)styryl)chlorobenzene, 4.8 g (50 mmol) of sodium tert-butoxide, 2.2 g (20 mmol) of p-toluidine, 3.7 mg (0.010 mmol) of [PdCl(allyl)]$_2$, and 16 mg (0.040 mmol) of 1,1-diphenyl-2-(dicyclohexylphosphino)propene were added to 40 ml of xylene, followed by heating to 100° C. After stirring for 4 hours, water was added, then toluene was added and the organic layer was extracted. After washing with water, the organic layer was concentrated, followed by recrystallization using a toluene-methanol solvent, to obtain 8.6 g of a yellow solid. An 8.4 g portion of the yellow solid was mixed with 60 ml of xylene, and 1.9 g (20 mmol) of sodium tert-butoxide, 2.8 g (8.0 mmol) of 1,4-bis(4-chlorostyryl)benzene, 2.9 mg (0.008 mmol) of [PdCl(allyl)]$_2$, and 13 mg (0.032 mmol) of 1,1-diphenyl-2-(dicyclohexylphosphino)propene were further added, followed by heating to 120° C. After stirring for 4 hours, water was added, then toluene was added and the organic layer was extracted. After washing with water, the organic layer was concentrated, followed by recrystallization using a toluene-ethyl acetate solvent, to obtain 9.5 g of a yellow solid (Compound 1-13). The yield was 61%.

1H NMR (CDCl$_3$): δ; 2.33 (s, 6H), 2.34 (s, 6H), 2.43 (s, 6H), 6.69 (d, J=15.3 Hz, 2H), 6.82 (d, J=11.1 Hz, 2H), 6.90-7.08 (m, 22H), 7.10 (d, J=8.6 Hz, 8H), 7.16-7.24 (m, 12H), 7.28 (d, J=8.4 Hz, 4H), 7.35-7.39 (m, 12H), 7.46 (s, 4H).

FD-MS([M]+): found m/z 1312.6634 [C100H84N2]+ (calculated; 1312.6523, −8.49 ppm)

mp 170-172° C.

Example 6

Synthesis of Compound (1-17)

Under a nitrogen atmosphere, 8.9 g (20 mmol) of 4-(4'-(4'',4''-bis(4'''-methylphenyl)-1'',3''-butadienyl)styryl)chlorobenzene, 2.4 g (25 mmol) of sodium tert-butoxide, 2.7 g (20 mmol) of 2,4-dimethylaniline, 7.3 mg (0.020 mmol) of [PdCl(allyl)]$_2$, and 31 mg (0.080 mmol) of 1,1-diphenyl-2-(dicyclohexylphosphino)propene were added to 40 ml of xylene, followed by heating to 110° C. After stirring for 3 hours, water was added, then toluene was added and the organic layer was extracted. After washing with water, the organic layer was concentrated, followed by recrystallization using a toluene-methanol solvent, to obtain 8.5 g of a yellow solid. A 6.5 g portion of the yellow solid was mixed with 40 ml of xylene, and 1.4 g (15 mmol) of sodium tert-butoxide, 2.1 g (6.0 mmol) of 1,4-bis(4-chlorostyryl)benzene, 4.4 mg (0.012 mmol) of [PdCl(allyl)]$_2$, and 19 mg (0.048 mmol) of 1,1-diphenyl-2-(dicyclohexylphosphino)propene were further added, followed by heating to 120° C. After stirring for 7 hours, water was added, then toluene was added and the organic layer was extracted. After washing with water, the organic layer was concentrated, followed by recrystallization using a toluene-ethyl acetate solvent, to obtain 5.0 g of a yellow solid (Compound 1-17). The yield was 50%.

1H NMR (CDCl$_3$): δ; 2.00 (s, 6H), 2.34 (s, 6H), 2.35 (s, 6H), 2.43 (s, 6H), 6.68 (d, J=15.3 Hz, 2H), 6.82 (d, J=11.1 Hz, 2H), 6.90-7.23 (m, 40H), 7.27 (d, J=8.4 Hz, 4H), 7.33-7.38 (m, 12H), 7.44 (s, 4H).

FD-MS([M]+): found m/z 1340.6928 [C102H88N2]+ (calculated; 1340.6947, −1.45 ppm)

mp 255-257° C.

Example 7

In 85 parts by weight of tetrahydrofuran, 15 parts by weight of a polycarbonate resin "TS-2020" (manufactured by Teijin Chemicals Ltd.) as a binder resin and 15 parts by weight of Compound (1-1) obtained in Example 1 were mixed and dissolved. The solution was applied onto a sheet, which had been prepared by vapor deposition of aluminum onto a polyethylene phthalate (PET) film, with a doctor blade, followed by drying at 80° C. for 3 hours, to form a charge transport layer (thickness: approximately 18 μm).

A translucent gold electrode was vapor deposited onto the charge transport layer, and the charge carrier mobility was measured. The carrier mobility was measured by the Time-of-Flight method (Hiroaki Tanaka, Yasuhiro Yamaguchi, Masaaki Yokoyama: DENSHI SHASHIN GAKKAISHI (Electrophotography), 29, 366(1990)) using a nitrogen gas laser with a pulsed half width of 0.9 sec and a wavelength of 337 nm as a light source. Table 1 shows the measurement results at 25° C. and 25 V/μm.

Examples 8 to 10

In the same manner as in Example 7, charge transport layers were formed by using Compound (1-7) obtained in Example 3, Compound (1-9) obtained in Example 4, and Compound (1-17) obtained in Example 6, and the charge carrier mobility was measured. Table 1 shows the results.

Comparative Examples 1 and 2

In the same manner as in Example 7, charge transport layers were formed by using Comparative Compound (1) or Comparative Compound (2), and the charge carrier mobility was measured. Table 1 shows the results.

Note that Comparative Compound (1) was synthesized by a method described in Japanese Examined Patent Application Publication No. Hei 7-21646. Comparative Compound (2) was synthesized by a method described in a document (J. Org. Chem., 2000, 65, 5327).

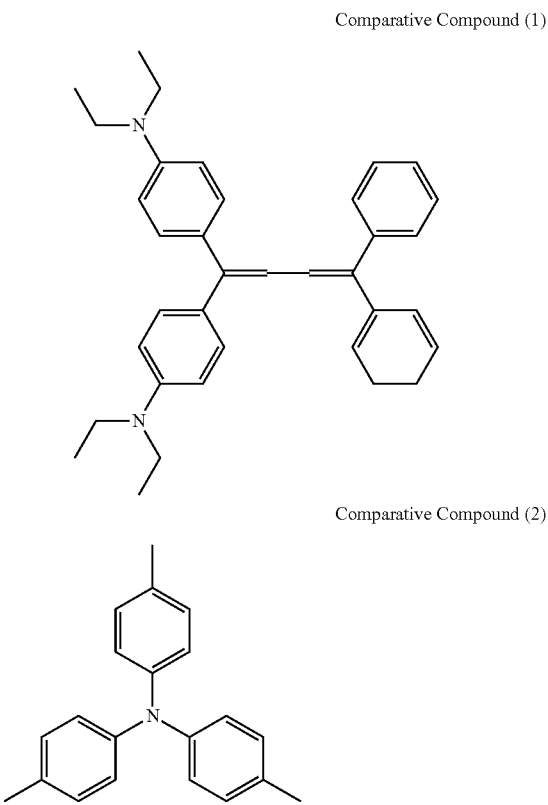

Comparative Compound (1)

Comparative Compound (2)

TABLE 1

| | | Charge carrier mobility (cm$^2$/Vs) |
|---|---|---|
| Example 7 | Compound (1-1) | 12.8 × 10$^{-5}$ |
| Example 8 | Compound (1-7) | 10.8 × 10$^{-5}$ |
| Example 9 | Compound (1-9) | 16.0 × 10$^{-5}$ |
| Example 10 | Compound (1-17) | 11.8 × 10$^{-5}$ |
| Comparative Example 1 | Comparative Compound (1) | 0.3 × 10$^{-5}$ |
| Comparative Example 2 | Comparative Compound (2) | 0.7 × 10$^{-5}$ |

As is apparent from Table 1, it can be seen that the compounds of the present invention have larger charge carrier mobilities and higher hole transporting abilities than the compounds (Comparative Compound (1) and Comparative Compound (2)), which are commonly and widely used as electrophotographic photoreceptors.

Example 11

A solution prepared by dissolving 0.375 parts by weight of a polyamide resin "FINE RESIN FR-104" (manufactured by Namariichi Co., Ltd.) in methanol and adjusting the total to 25 parts by weight was applied onto an aluminum plate and dried at 105° C. for 1 hour, to form an underlayer.

To a binder solution obtained by dissolving 15 parts by weight of a butyral resin "S-LEC BH-3" (manufactured by Sekisui Chemical Co., Ltd.) in 750 parts by weight of cyclohexanone, 22.5 parts by weight of phthalocyanine "Fastogen Blue 8120BS" (manufactured by Dainippon Ink and Chemicals, Incorporated) was added, and dispersed by using a vibration mill together with glass beads for 4 days. The dispersion was applied onto the underlayer and dried at 105° C. for 1 hour, to form a charge generation layer.

12 parts by weight of a polycarbonate resin "Iupilon Z-200" (manufactured by Mitsubishi Engineering-Plastics Corporation) as a binder resin and 8 parts by weight of Compound (1-1) obtained in Example 1 were mixed and dissolved in tetrahydrofuran with which the total was adjusted to 100 parts by weight. The solution was applied onto the charge generation layer with a doctor blade, and dried at 80° C. for 2 hours, to form a charge transport layer. A functionally-separated multilayer type electrophotographic photoreceptor was obtained by using the obtained charge generation layer and charge transport layer.

The photoreceptor characteristics of the thus obtained electrophotographic photoreceptor were measured by using an electrostatic recording tester "EPA-8300A" (manufactured by Kawaguchi Electric Works.) by the static method. Specifically, the electrophotographic photoreceptor was charged by performing corona discharge at −6 kv, and the surface potential $V_0$ (Unit: −v) was measured. The electrophotographic photoreceptor was held in a dark place for 5 seconds (surface potential $V_i$ (Unit: −v)) and dark decay retention L/D($V_i$/$V_0$ (Unit: %)) was determined. After that, the electrophotographic photoreceptor was irradiated with 0.2 μW laser light at 780 nm to determine the half decay exposure $E_{1/2}$ (mJ/cm$^2$), which was the amount of light exposure necessary to reduce the surface potential $V_i$ by half, and the $E_{1/6}$ (mJ/cm$^2$), which was the amount of light exposure necessary to reduce the surface potential $V_i$ to ⅙, and then the surface residual potential $V_r$ (Unit: −v) was determined after irradiation for 5 seconds. Table 2 shows the results.

Examples 12 and 13

Electrophotographic photoreceptors were prepared and the photoreceptor characteristics thereof were measured in the same manner as in Example 11, except that the charge transport layers were prepared by using Compound (1-9) and Compound (1-17) Table 2 shows the results.

Comparative Examples 3 and 4

Electrophotographic photoreceptors were prepared and the photoreceptor characteristics thereof were measured in the same manner as in Example 11, except that charge transport layers were prepared by using Comparative Compound (3) (manufactured by Takasago International Corporation, "CTC-191") or Comparative Compound (4) (manufactured by Takasago International Corporation, "CT-4"). Table 2 shows the results.

Comparative Compound (3)

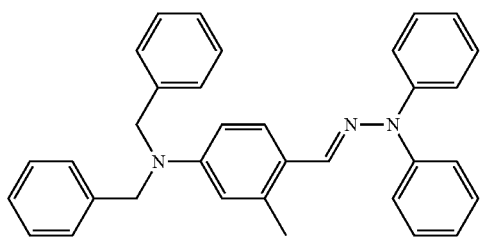

Comparative Compound (4)

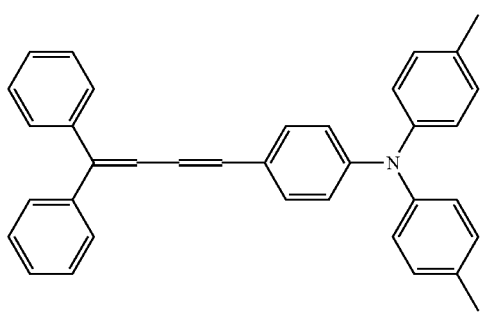

tials ($V_r$) than the electrophotographic photoreceptors using Comparative Compound (3) and Comparative Compound (4).

Example 14

Compound (1-1) was dissolved in 1 g of tetrahydrofuran at 25° C. Table 3 shows the weight of the compound completely dissolved.

Examples 15 and 16

In the same manner as in Example 14, experiments were conducted by using Compound (1-4) or (1-9). Table 4 shows the results.

Comparative Example 5

In the same manner as in Example 14, experiments were conducted by using Comparative Compound (5) which was a compound described in Japanese Patent Application Publication No. Hei 3-149560. Table 3 shows the results.

Comparative Compound (5)

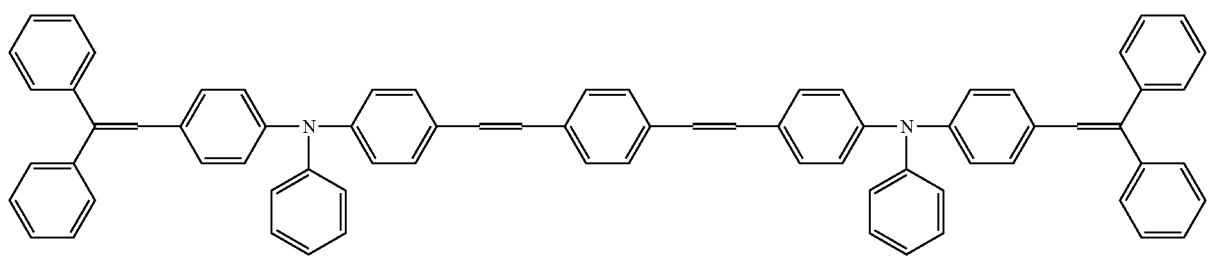

TABLE 2

| | | $V_0$ (-V) | $V_1$ (-V) | L/D (%) | $V_r$ (-V) | $E_{1/2}$ (mJ/ cm$^2$) | $E_{1/6}$ (mJ/ cm$^2$) |
|---|---|---|---|---|---|---|---|
| Example 11 | Compound (1-1) | 443 | 434 | 98 | 67 | 0.05 | 0.13 |
| Example 12 | Compound (1-9) | 419 | 410 | 98 | 56 | 0.05 | 0.12 |
| Example 13 | Compound (1-17) | 423 | 416 | 98 | 50 | 0.04 | 0.10 |
| Comparative Example 3 | Comparative Compound (3) | 485 | 479 | 99 | 144 | 0.07 | 0.16 |
| Comparative Example 4 | Comparative Compound (4) | 489 | 484 | 99 | 123 | 0.06 | 0.16 |

As is apparent from Table 2, it can be seen that the electrophotographic photoreceptors using the compounds of the present invention have better sensitivities (smaller $E_{1/2}$ values and smaller $E_{1/6}$ values), and lower residual poten-

TABLE 3

| | | Solubility (g/g tetrahydrofuran) (25° C.) |
|---|---|---|
| Example 14 | Compound (1-1) | 0.16 |
| Example 15 | Compound (1-4) | 0.13 |
| Example 16 | Compound (1-9) | 0.14 |
| Comparative Example 5 | Comparative Compound (5) | 0.03 |

As is apparent from Table 3, the compounds of the present invention have excellent solubility, making it possible to form high-concentration organic thin films.

INDUSTRIAL APPLICABILITY

The triphenylamine derivative represented by general formula (1) of the present invention is industrially excellent, because it is useful as a charge transport material, and further makes it possible to provide an electrophotographic photoreceptor which exhibits a high carrier mobility, and has good mechanical characteristics, such as high sensitivity and low residual potential.

The triphenylamine derivative represented by general formula (1) of the present invention has a high charge transport ability, and hence can also be used for organic electroluminescence, organic transistors, organic solar cells, and the like.

The invention claimed is:

1. A triphenylamine derivative represented by general formula (1):

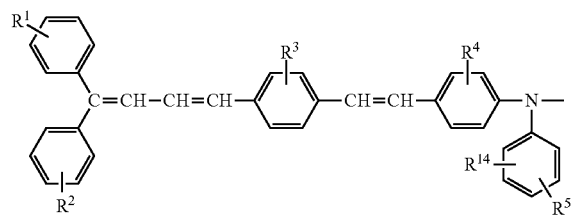

(1)

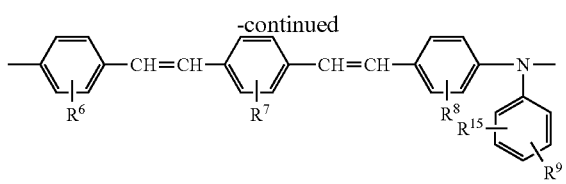

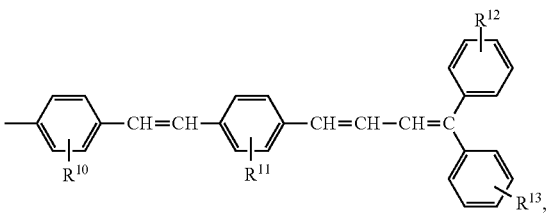

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ each independently represent a hydrogen atom, a substituted or unsubstituted alkyl group, or a substituted or unsubstituted alkoxy group.

2. The triphenylamine derivative according to claim 1, which is represented by general formula (1'):

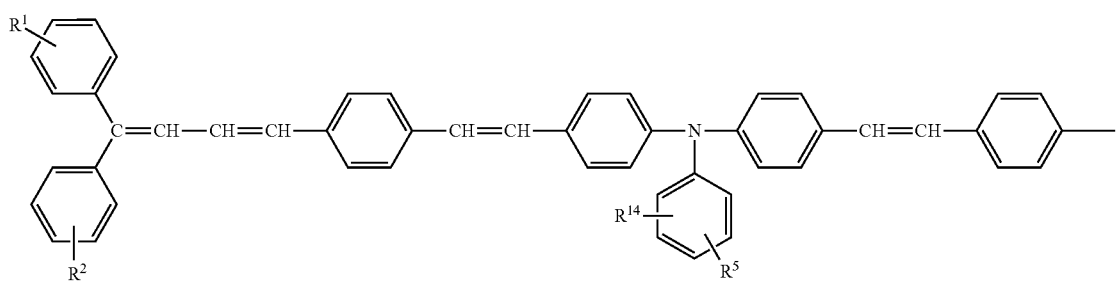

(1')

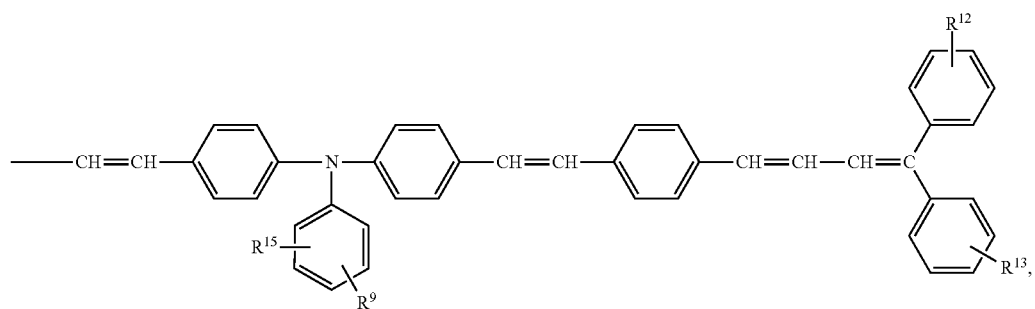

wherein $R^1$, $R^2$, $R^5$, $R^9$, $R^{12}$, $R^{13}$, $R^{14}$, and $R^{15}$ each independently represent a hydrogen atom, an alkyl group having 1 to 6 carbon atoms, or an alkoxy group having 1 to 6 carbon atoms.

3. A charge transport material comprising the triphenylamine derivative according to claim 1.

4. An electrophotographic photoreceptor comprising the charge transport material according to claim 3.

5. A charge transport material comprising the triphenylamine derivative according to claim 2.

6. An electrophotographic photoreceptor comprising the charge transport material according to claim 5.

* * * * *